United States Patent [19]

Gamblin

[11] Patent Number: 5,162,511
[45] Date of Patent: Nov. 10, 1992

[54] NITROSATING AND DIAZOTIZING REAGENTS AND REACTIONS

[76] Inventor: Rodger L. Gamblin, 8 Springhouse Rd., Dayton, Ohio 45409

[21] Appl. No.: 858,956

[22] Filed: Mar. 27, 1992

Related U.S. Application Data

[62] Division of Ser. No. 649,762, Feb. 1, 1991.

[51] Int. Cl.$^5$ .................. C09B 41/00; C09B 29/32
[52] U.S. Cl. ........................... 534/579; 534/580
[58] Field of Search .................. 534/579, 580

[56] References Cited

U.S. PATENT DOCUMENTS

| | | | |
|---|---|---|---|
| 3,793,305 | 2/1974 | Balon | 534/579 |
| 3,928,314 | 1/1975 | Rochat et al. | 534/579 |
| 4,118,384 | 10/1978 | Mölls et al. | 534/579 |
| 4,496,481 | 1/1985 | Wheeler | 534/579 |

Primary Examiner—Marianne M. Cintins
Assistant Examiner—John D. Peabody, III
Attorney, Agent, or Firm—Wood, Herron & Evans

[57] ABSTRACT

Sulfonic acids are reacted with sodium nitrite to form new compositions specifically nitrosyl sulfonates. The nitrosyl sulfonates are useful in reacting with a dye base to form a diazo composition which can in turn react with a coupling agent to form a diazo dye. The nitrosyl sulfonate can also be used to react with an aromatic composition to nitrosoate an aromatic composition. These reactions are particularly useful in the formation of a dispersed dye because the dye can be formed directly in a nonpolar organic solvent and can be used without purification of the dye product. Particularly useful is the nitrosyl dodecyl benzene sulfonate since the formed product is soluble in nonpolar solvents and all reaction products remain in solution and aid with the dyeing of fabrics.

4 Claims, No Drawings

NITROSATING AND DIAZOTIZING REAGENTS AND REACTIONS

This is a division, of application Ser. No. 07/649,762, filed Feb. 1, 1991.

BACKGROUND OF THE INVENTION

Diazotization is a reaction between a primary aromatic amine and nitrous acid to give a diazo compound. The most common method of diazotizing a primary aromatic amine is by slow addition of an aqueous solution of sodium nitrite to a solution of the amine and dilute mineral acid held at 0° to 10° C. Not only can amino groups on benzene, naphthlene, and their substituted derivatives be diazotized, but heterocylic amines such as amino thiazoles and certain amino pyridines will also undergo the reaction. There are many detailed reviews of diazo chemistry, for example, *Ullmann's Encyclopedia of Industrial Chemistry*, Vol. A8, page 505 (VCH Publishers, New York, N.Y.).

Sodium nitrite, a primary diazotizing reagent, is quite stable by itself. The formed diazo compounds or salts, however, are relatively unstable but are very useful in other reactions. The diazo group on the aromatic ring may readily be replaced with moieties or radicals such as bromo, chloro, cyano and other groups. Diazo salts will couple to active sites on the ring of activated aromatic compounds such as phenols, naphthols, amines and certain other compounds to form diazo dyes. This reaction is the basis of diazo chemistry's most important commercial use. It is generally believed that the reaction mechanism is based on the attack of the strongly electrophilic diazo ion on a position of high electron density of a nucleophillic coupling component.

Electronegative substituents on the ring of the diazo compound increases its coupling power and the diazo compound of trinitroaniline, which is the most reactive diazo compound in this respect, will couple even with mesitylene. Diazo compounds can also couple with phenol and naphthyl ethers, compounds containing reactive methylene groups such as acetoacetanilides, nitriles, pyrazolinones, nitroparaffins, certain unsaturated hydrocarbons, and heterocyclic compounds of high electron density.

In the case of disperse dyes, the diazo base, that is, the primary aromatic amine that is to be diazotized is most often aniline with one to three strongly electron withdrawing substituents in the 2, 4 or 6 positions. The 4 position is usually the nitro group and the 2 and 6 positions are generally occupied by either hydrogen, nitro, chloro, bromo or cyano groups. Heterocyclic compounds such as substituted 2 amino-benzothiazoles, 2 amino thiazoles, and 4 amino pyridines are also used as diazo bases for dispersed dyes. In the case of 4 nitroaniline, and 2 chloro-4 nitro aniline, the diazo salt is formed by heating the amine in water with four or more mole equivalents of hydrochloric acid until the amine dissolves, then cooling to ice temperature. At this point a mole equivalent of sodium nitrite dissolved in ice water is slowly added and the mixture allowed to diazotize.

In the case of aniline with two nitro or cyano groups, aniline with three or more substituents as above, or most heterocyclics, diazotization can no longer be carried out in aqueous solution and is most often carried out with nitrosylsulfuric acid (sodium nitrite dissolved in an excess of sulfuric acid) in sulfuric acid or sulfuric acid in a lower carboxylic acid such as acetic or proprionic. In such a case an appropriate amount of sodium nitrite is dissolved in cold sulfuric acid and added to a solution of the amine in acid. The cold mix is warmed to 40°–60° C. and held until a drop into cold water totally dissolves. This mix is then mixed with crushed ice while stirring rapidly and the resulting cold diazo solution filtered.

Once the diazo salt is formed by either process, it is added to a cold solution of coupling compound (coupler). This coupler is most often a tertiary aromatic amine (for dispersed dyes) which is dissolved in solution of water or water and a solvent but contains sufficient base such as, for example, sodium acetate or sodium carbonate to achieve only slightly acidic pH when mixed with the acetic diazo solution.

After the two solutions are mixed, the dye precipitates and after a time the remaining contaminated salt solution is washed away and the dye filtered off. The dye is then mixed with dispersing agents and subjected to extensive grinding, usually in a sandmill, mixed with more dispersing agents or diluents and then either dried or made into a paste for use.

Though there is nothing very complex about these procedures and though yields are generally good, the waste generated, the washing, the filtering, the grinding, and the mixing all contribute to the cost of the process.

SUMMARY OF THE INVENTION

The present invention is premised on the realization that a unique diazotizing/nitrosating agent can be formed by reacting an organic sulfonate with an alkali or alkaline earth metal nitrite under acidic conditions. This diazotizing agent is then the nitrosyl sulfonate.

More particularly, the present invention is premised on the realization that this nitrosyl sulfonate is useful in diazotization of primary aromatic amines which can in turn be used to react with coupling agents to form organic diazo dyes.

Further, the present invention is premised on the realization that substantial waste and cost can be avoided by directly forming a solution of nitrosyl sulfonate by reacting a metal nitrite with an organic sulfonic acid in an organic solvent. The nitrosyl sulfonate in turn reacts with a primary aromatic amine to form the diazo salt which with suitable organic sulfonates is also soluble in the organic solvent. A suitable coupling agent which is generally soluble in the organic solvent can be added. The diazo dye forms in solution. This solution of the dye can then be used without further purification.

The present invention is further premised on the realization that such a solution of diazo dye can be formed in a solvent which acts as a dyeing assist composition further facilitating the use of the dye system in dyeing fabrics and material.

In a preferred embodiment, the diazotizing agent is a new compound, a nitrosyl sulfonate, specifically nitrosyl dodecylbenzene sulfonate. The present invention will be further appreciated in light of the following detailed description.

DETAILED DESCRIPTION

The present invention encompasses the reaction of an alkali or alkaline earth metal nitrite with a sulfonic acid to form a nitrosyl sulfonate. The nitrosyl sulfonate can react with a coupling agent which is an activated aromatic compound to form a nitroso dye. Alternatively, the nitrosyl sulfonate in solution can react with a primary aromatic amine, referred to as a dye base to form a diazo sulfonate. This compound, which is relatively unstable, remains in solution. The diazo sulfonate can in turn react with a coupling agent which is an activated aromatic compound to form a diazo dye. Alternately, the diazo sulfonate can be used to react with other compounds such a acetoacetanilides, pyrazolinones, conjugated hydrocarbons, heterocyclic compounds and so forth.

The formation of the nitrosyl sulfonate is shown in the formula one below.

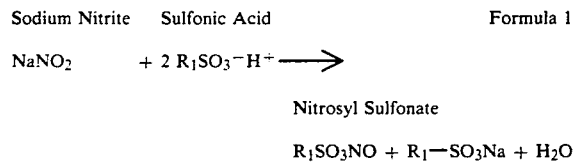

Sodium Nitrite    Sulfonic Acid                    Formula 1

$$NaNO_2 + 2\, R_1SO_3^-H^+ \longrightarrow$$

Nitrosyl Sulfonate $$R_1SO_3NO + R_1\text{—}SO_3Na + H_2O$$

For use in the present invention, the sulfonic acid is one which is soluble in organic solvents such as toluene, benzene, naphthalene, xylene, alpha-methyl naphthalene, perchoroethylene, etc. This sulfonic acid can be an alkyl sulfonic acid, wherein $R_1$ represents a $C_{10}$–$C_{20}$ alkyl and more particularly a $C_{16}$–$C_{20}$ alkyl. It can be an aryl sulfonic acid such as phenyl, naphthyl, anthryl, phenalenyl and phenanthryl sulfonic acids. The aromatic group can be substituted or unsubstituted. The sulfonic acid can also be a polymer such as the condensation polymer between formaldehyde and an aromatic sulfonic acid such as naphthalene sulfonic acid. It could also be an addition polymer with sulfonic groups appended to the chain such as sulfonated polystyrene ethylene copolymer, for example. $R_1$ of the aromatic sulfonic acids can be further represented by the formula:

$R_2$—Ar—

Where $R_2$ represents 1 to 5 substituents attached to the aromatic ring Ar and is selected from the group $C_1$–$C_{20}$ alkyl, hydrogen, nitro, amino, alkyl aryl, aryl, halide, carboxyl, hydroxyl, cyano, sulfhydryl, aryloxy where the aryl groups substituents can be phenyl, naphthyl, anthryl or phenanthrenyl. For example, for dodecylbenzene sulfonic acid, $R_2$ represents a dodecyl group and Ar represents phenyl.

Specific sulfonic acids suitable for use in the present invention include paratoluene sulfonic acid, methane sulfonic acid, naphthalene sulfonic acid and its condensates with formaldehyde, and dinonylnaphthlene sulfonic acid. Dodecylbenzene benzene sulfonic acid or xylene sulfonic acids are preferred for dispersed dyes because they act as dispersing agents or solubilizing agents for the dyes formed in the dye making process which are dispersed or solubilized in water for use as dispersed dyes. Dodecylbenzene benzene sulfonic acid is most preferred since it is inexpensive, relatively environmentally safe and readily available. It also, as noted above, is a powerful surfactant and dispersing agent and thus useful in a final formula. This compound forms the preferred nitrosating agent 4-dodecylbenzene nitrosylsulfonate.

Alkali metal or alkaline earth metal salts of nitrous acid, for example, sodium or calcium nitrite, are readily available, stable and commonly used as a source of nitric acid for diazo reactions. Sodium nitrite is preferred.

The nitrosyl sulfonate is formed by mixing two molar equivalents of the sulfonic acid $R_1SO_3H$ with a molar equivalent of nitrite salt such as sodium nitrite in a low polarity organic solvent such as toluene or xylene. If a dispersed dye is being formed, the preferred solvent is a solvent that acts as a dyeing assistant for the formed dispersed dye. Dyeing assistants are known and one particular dyeing assistant is alpha methylnaphthalene. The solvent, the sulfonic acid and sodium nitrite are mixed at room temperature to 60° C. for a period of up to 6 hours.

Low polarity solvents include aliphatic acids, aromatic hydrocarbons, chlorinated hydrocarbons, cycloparaffins, alkyl aryl hydrocarbons, and so forth. In such material, due to their low solubility constants, the sulfonic acids are extremely strong and readily protonate dye bases that presently are protonated only by such very strong acids as concentrated sulfuric or concentrated sulfuric in lower carboxylic acids. By this means the procedures used with this invention are applicable to many different dyes, even those with difficult to diazotize bases, as discussed above, that currently use unconcentrated sulfuric acid as a diazotization medium. What is remarkable is that a mixture of sulfonic acid and low polarity solvent can be used to react with and dissolve sodium nitrite, an inorganic salt, to give a nitrosylsulfonic acid.

This reaction will be further appreciated in light of the following example 1.

EXAMPLE 1

65.2 grams (0.2 moles) of dodecylbenzene sulfonic acid (DBSA) from Pilot Chemical of Middletown, Ohio were mixed with 70 grams of toluene from Gem City Chemical of Dayton, Ohio. 7 grams of sodium nitrite from Pfaltz and Bauer, Inc. of Waterbury, Conn. were added and the mix stirred at room temperature for a period of 6 hours. Initially, the mix darkened and after a few minutes a small amount of nitrogen dioxide formed over the stirring mix. After about an hour, the mix began to lighten until, after the six hours of stirring, the mix is about the same color or slightly lighter than the initial DBSA toluene mix. The sodium nitrite is completely dissolved.

The formed nitrosyl dodecylbenzene sulfonate is not isolated and is used in solution.

The nitrosyl sulfonate can then be used to react with a dye base to form a diazo sulfonate or can be used as a nitrosating agent with secondary and tertiary aromatic amines and other reactive compounds.

This diazotization reaction is further shown in formula 2.

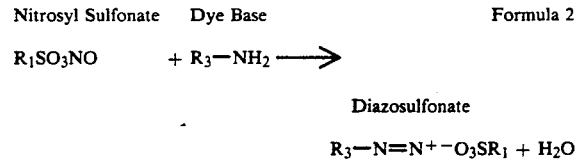

Nitrosyl Sulfonate    Dye Base                    Formula 2

$$R_1SO_3NO + R_3\text{—}NH_2 \longrightarrow$$

Diazosulfonate $$R_3\text{—}N\!=\!N^+\,{}^-O_3SR_1 + H_2O$$

The dye bases suitable for use in this invention are those typically used in the formation of diazo dyes. These dye bases can be primary aromatic amines where $R_3$ represents an unsubstituted or a substituted aryl group $R_4$-Ar wherein Ar represents phenyl, naphthyl, anthryl, phenalenyl and phenanthryl. These can be unsubstituted or substituted with a variety of different substituents $R_4$ such as $C_1$-$C_{20}$ alkyl, aryl, alkyl aryl, substituted alkyl, aryl or alkyl aryl, nitro, halide, cyano, sulfonic, carboxyl, amine or substituted amine, hydrocarbon or substituted hydrocarbon and so forth. Heterocyclic amines, such as amino thiazoles, and certain amino pyridines will also undergo this reaction as dye bases. Particularly useful dye bases for dispersed dyes include paranitroaniline, 2,4-dinitroaniline, 2 chloro-4-nitroaniline, 2,6 dichloro-4-nitroaniline, 2-cyano-4-nitroaniline, 6 chloro-2,4-dinitroaniline, 6 bromo-2,4-dinitroaniline, 2 bromo-4-nitroaniline, 2 amino-5-nitro thiazole, 2 amino-6-nitro benzothiazole, 2 amino-3,5-dinitrothiophene, 2 amino benzoisothiazole, and sulfanilamide.

This reaction may be conducted at room temperature by adding the dye base to the solution containing the nitrosyl sulfonate or may be conducted at temperatures of up to about 75° C. to increase the rate of reaction. The permitted higher temperature depends upon the base being diazotized. Generally weak bases are more robust at higher temperatures while weak bases tend to decompose when diazotized and heated (when concentrated they may explode when heated).

To form a dye, the diazo sulfonate is reacted with a coupling agent. This reaction is referred to as the coupling reaction. The coupling reaction is shown in Formula 3.

Diazo Sulfonate   Coupling Agent   Dye   Formula 3

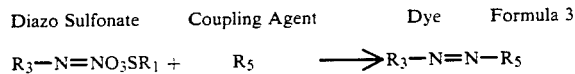

$R_3-N=NO_3SR_1 + R_5 \longrightarrow R_3-N=N-R_5$

The diazotization reaction and the coupling reaction are preferably conducted in a one-pot procedure. The dye base is combined with a non-polar solvent, alkali metal nitrite, and organic sulfonic acid. The result is mixed until most of the nitrite is dissolved, and the coupling agent is then added.

With certain bases and coupling agents, it is convenient to place the base, sulfonic acid, coupling agent, solvent, and sodium nitrite together and stir at a temperature of 5° to 90° C. (depending on the dye to be formed) for a period of time. For such a reaction to be successful, the coupling agent must generally be a tertiary amine or phenolic material that does not nitrosate readily, and the base must be of a nature that it does not readily couple to itself.

In certain cases, industry practice dictates that no solvent be carried along with the dye. In such situations, low boiling point solvents such as methylene chloride, chloroform, butane or heptane may be used and distilled off from the mix after the dye is formed.

For use in the present invention, the coupling agent, $R_5$, can be any coupling agent which is suitable for use in the formation of a diazo dye. These are a class of compounds which are well known to those skilled in the art. For example, such agents may be activated aromatic compounds. By activated is meant that the aromatic ring has a relatively high election density at the site for coupling due to activating substituents suitably placed on the ring (such as an aromatic amine or phenolic compound substituted in the para position). Alternatively suitable coupling agents are aliphatic compounds with an activated hydrogen such as acetoacetanilide, certain pyrimidines or pyrazolinones. Specific compositions include: N,N-diethylaniline, N-(2-hydroxyethyl)-N-ethylaniline, N-(2-cyanoethyl)-N-ethylanaline, beta-naphthol, N,N-bis(2 hydroxyethyl) aniline, N,N-bis(2 cyanoethyl)aniline, 4-methoxy-m bis(acetoxyethylamino)acetanilide, N,N bis(2 hydroxethyl) m toluidine, m-N,N bis (acetoxyethyl)acetanilide, and N-acetoxyethyl-N-cyanoethylaniline.

The invention will be further appreciated in light of the following detailed examples.

EXAMPLE 2

13.8 grams of p-nitroaniline from Aldrich Chemical Co. of Milwaukee, Wis. and 16.5 grams of N-(2-hydroxyethyl)-N-ethylanaline from Pfaltz and Bauer, Inc. Division of Aceto Corporation of Waterbury, Conn., were added to a mixture of 80.0 grams of toluene from Gem City Chemical Company of Dayton, Ohio and 49.0 grams of dodecylbenzene sulfonic acid from Pilot Chemical of Middletown, Ohio. The mix was stirred for about one hour during which time the temperature declined to near room temperature. While stirring this mix 7.0 grams of dry sodium nitrite from Pfaltz and Bauer were added and stirring continued for 8 hours. The mixture turned a beautiful red and is a mix of surfactant, toluene and Color Index Disperse Red 1. (The Color Index is a publication of the American Association of Textile Colorists and Chemists in Charlotte, N.C. and lists and names the various chemicals used as dyes.) Disperse Red 1 is, for example, listed in the Color Index as CI 11110.

EXAMPLE 3

Two grams of the material made in Example 2 were added to 200 grams of warm water while stirring and the mix was heated to 95° C. About two grams of 37% ammonia from Gem City Chemical of Dayton, Ohio were added. Three samples of 100% polyester fabric were added to the bath and maintained there for sixty minutes. The result was an intense scarlet dyeing of the polyester sample.

EXAMPLE 4

The procedures described in Example 2 were followed for Example 4 except that 17.4 grams of N-(2 cyanoethyl)-N-ethyl aniline from Sandoz Chemical Corporation of Charlotte, N.C. were substituted for the N-(2-hydroxyethyl)-N-ethyl aniline of Example 1. The result was a bright orange solution containing slightly less than 20% of Disperse Orange 25.

EXAMPLE 5

13.8 grams of p-nitroaniline from Aldrich were added to 70 grams of alpha-methylnaphthylene from Crowley Chemical Company, New York, N.Y. and 49 grams of dodecylbenzene sulfonic acid from Pilot and the mixture was stirred at 45° C. until all ingredients had dissolved. Seven grams of NaNO$_2$ from Pfaltz and Bauer were then added and the mix allowed to stir for twenty minutes and heated to 55° C. at which time 9.3 grams of aniline from Kessler Chemical of Pipersville, Pa. was added. The mixture immediately turned bright orange but was allowed to stir for six hours at about 65° C. The resulting material produced a bright orange dyeing on polyester similar in shade to Disperse Orange 3 purchased from Aldrich Chemical.

EXAMPLE 6

The procedures of Example 2 were followed exactly except that 16.2 grams of 2-chloro-4-nitro aniline from Aldrich Chemical was substituted for the p-nitroaniline of Example 1. The resulting red solution was used to dye polyester a rich bluish red.

EXAMPLE 7

2.70 grams of 6-bromo-2,4-dinitroaniline from Atlantic Chemical Company of Nutley, N.J. were added to 50 grams of toluene along with 5 grams of dodecylbenzene sulfonic acid and 6.1 grams of 60% active 4-methoxy-m-(bis(acetoxy-ethyl)amino) acetanilide also from Atlantic. This mix was stirred until it came to room temperature and 0.7 grams of sodium nitrite from Pfaltz and Bauer was added. A rich purple red solution formed and was stirred for a few hours. The resulting solution was used in a procedure similar to that described in Example 2 to yield a blue dyeing of polyester.

EXAMPLE 8

3.0 grams of the solution made in Example 4 were added to 300 grams of water and brought to a near boil. A 10×25 cm swatch of white polyester fabric was added to the dye bath and boiled for five minutes. The material became a beautiful orange fast to washing and light.

The nitrosyl sulfonate of the present invention is also useful as a nitrosating agent for aromatic compositions such as aromatic tertiary amines, aromatic alcohols and other compounds previously described as coupling agents. This reaction is an electrophilic aromatic substitution reaction. It is caused by the electrophilic attack by $+NO$ with displacement of $H^+$. This attack occurs at the position of highest electron availability as modified by steric effects.

The nitrosation reaction is shown by the following formula.

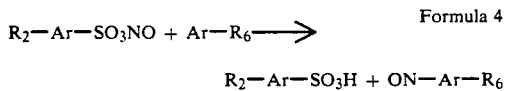

Formula 4

Wherein Ar is phenyl, naphthyl, phenanthryl or anthryl and $R_6$ is $-OR_7$ or $-NR_8R_9$ in a position ortho or para to the point of attack of the nitrosyl group. $R_7$, $R_8$ and $R_9$ are hydrogen substituted and unsubstituted alkyl, substituted aryl or substituted alkyl aryl moieties. The application of formula 4 is shown in Example 9.

EXAMPLE 9

Seven grams of sodium nitrite from Pfaltz and Bauer along with 15 grams of N,N diethylaniline also from Pfaltz and Bauer, and 32.6 grams of dodecylbenzene sulfonic acid from Pilot was added to 100 grams of toluene from Gem City Chemical Company and the mix allowed to stir with warming to about 50° C. for 6 hours. The resulting solution is a bright greenish yellow dye solution.

As can be seen from the preceding description, the present invention provides a unique composition, specifically a nitrosyl sulfonate. By use of the nitrosyl sulfonate and particularly an alkyl aryl nitrosyl sulfonate, one may substantially reduce the cost and wastes associated with formation of diazo dyes. Further, this nitrosyl sulfonate can be used to nitrosate activated aromatic compositions.

The preceding has been a description of the present invention along with the best mode of practicing the invention currently known. However, the invention itself is to be defined by the appended claims wherein

We claim:

1. A method of using an organic sulfonic acid comprising reacting said sulfonic acid, a metal nitrite, a dye base and a coupling agent in an organic solvent to thereby form a dispersed diazo dye, wherein said metal nitrate is reacted with said sulfonic acid to form a nitrosyl sulfonate and wherein said nitrosyl sulfonate is reacted with said dye base and said coupling agent.

2. The method claimed in claim 1 wherein said dye base is selected from the group consisting of aniline, p-nitroaniline, 2,4 dinitroaniline, 2 chloro-4-nitroaniline, 2 cyano-4-nitroaniline, 2,6 dichloro-4-nitroaniline, 6-bromo-2,4 dinitroaniline, 6 chloro-2,4 dinitroaniline, 2 bromo-4-nitroaniline, 2 amino-5-nitro thiazole, 2 amino-6-nitro benzothiazole, 2 amino 3,5 dinitrothiophene, 2 amino benzoisothiazole and sulfanilamide.

3. The method claimed in claim 2 wherein said coupling agent comprises a composition selected from the group consisting of activated aromatic compositions, and aliphatic compositions having an active hydrogen.

4. The method claimed in claim 3 wherein said coupling agent is selected from the group consisting of phenol, acetoacetanilide, pyrimidine, pyrazolinone, N,N-diethylaniline, N-(2-hydroxyethyl)-N-ethylaniline, N-(2-cyanoethyl)-N-ethylanaline, beta-naphthol, N,N-bis(2-hydroxyethyl)aniline, N,N-bis(2-cyanoethyl)aniline, 4-methoxy-m bis(acetoxy-ethylamino)acetanilide, N,N bis(2-hydroxethyl)m toluidine, m-N,N is(acetoxyethyl)acetanilide, and N-acetoxyethyl-N-cyanoethylaniline.

* * * * *